United States Patent [19]

Merger et al.

[11] Patent Number: 4,767,857

[45] Date of Patent: Aug. 30, 1988

[54] PREPARATION OF CAPROLACTAM

[75] Inventors: Franz Merger, Frankenthal; Claus-Ulrich Priester, Meckenheim; Rolf Fischer, Heidelberg; Manfred Sauerwald, Roedersheim-Gronau, all of Fed. Rep. of Germany

[73] Assignee: BASF Aktiengesellschaft, Ludwigshafen, Fed. Rep. of Germany

[21] Appl. No.: 133,735

[22] Filed: Dec. 16, 1987

[30] Foreign Application Priority Data

Dec. 17, 1986 [DE] Fed. Rep. of Germany ....... 3643010

[51] Int. Cl.$^4$ ............................................ C07D 201/08
[52] U.S. Cl. ..................................................... 540/538
[58] Field of Search ........................................ 540/538

[56] References Cited

U.S. PATENT DOCUMENTS

3,857,510 12/1974 Rogic et al. .................... 540/538
4,470,928 9/1984 Kimura et al. .................. 540/538

FOREIGN PATENT DOCUMENTS

14563 8/1963 Japan ................................. 540/538

OTHER PUBLICATIONS

Mares, (1978) Ind. Eng. Chem. Process Des. Dev. 17(1): 9–17.

*Primary Examiner*—Robert T. Bond
*Attorney, Agent, or Firm*—Keil & Weinkauf

[57] ABSTRACT

Caprolactam is prepared by heating a 6-aminocaproic ester at 100°–320° C. in the presence of a reaction medium comprising an aromatic hydrocarbon which is liquid under reaction conditions and has a boiling point from 80° to 240° C., and isolating caprolactam from the reaction medium.

7 Claims, No Drawings

PREPARATION OF CAPROLACTAM

The present invention relates to a process for preparing caprolactam from 6-aminocaproic esters.

German Laid-Open Application DOS No. 2,249,993 describes a process wherein 6-aminocaproic esters are reacted in water at 250°–350° C. to give caprolactam. However, the process has the disadvantage that, as known from Industrial Engineering Chem. Proc. Design Development 17 (1978), 11, 6-aminocaproic acid is an intermediate in this reaction and therefore, as is evident from loc. cit., 15, the cyclization should be carried out at low concentrations to suppress the formation of oligomers. As a consequence, isolating the caprolactam from the dilute aqueous solutions is technically complicated.

Loc. cit., 10–11, also discloses the cyclization of ethyl 6-aminocaproate in ethanol at 150°–250° C. to give caprolactam. However, substantial amounts of dimers are formed as byproducts in this reaction, so that the yield leaves something to be desired.

In another process, described in German Laid-Open Application DOS No. 3,235,938, 6-aminocaproic esters are converted into caprolactam by heating at 180°–250° C. in a polyhydric alcohol having a boiling point higher than that of caprolactam for 0.5–5 hours, and the caprolactam is then separated by distillation from the reaction mixture obtained. This process has the disadvantage of relying on demanding solvents such as tetraethylene glycol, diglycerol, pentaerythritol or butanetriol, which are thermolabile. In addition, the reaction is not selective, but gives rise to byproducts (aminocaprolactam conversion products) and caprolactam oligomers, which need to be recycled.

Japanese Patent Application No. 14,563/1963 discloses a process wherein ethyl 6-aminocaproate is condensed at 160°–165° C. in boiling ethylene glycol to caprolactam in the course of 4 hours. This process has the disadvantage that the yield leaves something to be desired and, what is more, the caprolactam is technically complicated to isolate from the reaction medium.

It is an object of the present invention to provide a process for preparing caprolactam from a 6-aminocaproic ester in a short time in a high yield and high conversions without expensive solvent, and where the caprolactam is simple to separate off and which avoids recycling of byproducts and precipitates due to the formation of polymers of caprolactam.

We have found that this object is achieved in a process for preparing caprolactam by heating a 6-aminocaproic ester in the presence of an inert organic reaction medium which is liquid under reaction conditions and has a boiling point below that of caprolactam, by using an aromatic hydrocarbon having a boiling point from 80° to 240° C. as the reaction medium, maintaining a temperature from 100° to 320° C. and isolating caprolactam from the reaction medium.

The novel process has the advantage of giving high conversions in high yields. A further advantage of the process is that an inexpensive solvent is used and the caprolactam is easy to isolate. Furthermore, the novel process has the advantage of not forming products which need to be recycled, nor, to any appreciable extent, polymers which lead to deposits.

The cyclocondensation of 6-aminocaproic esters in hydrocarbons has not been described before. It is true that the possibility of using hydrocarbons having a boiling point above that of caprolactam is mentioned in said DOS No. 3,235,938, but is dismissed with the comment that an insoluble polymer is formed. In the same context, said reference warns against using a solvent having a boiling point below that of caprolactam by suggesting that byproducts are formed which undergo denaturing in the course of the distillative workup and therefore are unusable.

Preferred starting materials comprise 6-aminocaproic esters of alkanols of 1 to 10 carbon atoms, cycloalkanols of 5 to 8 carbon atoms or aralkanols of 7 to 10 carbon atoms. Suitable starting materials are for example the methyl, ethyl, n-propyl, n-butyl, cyclohexyl, cyclooctyl, benzyl and phenylethyl esters of 6-aminocaproic acid. Particular preference is given to alkyl 6-aminocaproates, in particular $C_1$-$C_3$-alkyl 6-aminocaproates. Methyl and ethyl 6-aminocaproate have become particularly important for industrial use.

The reaction is carried out at from 100° to 320° C., advantageously from 130° to 280° C., in particular from 180° to 280° C. In general, atmospheric pressure is maintained, but preferably a superatmospheric pressure, for example up to 30 bar, is employed to ensure that the reaction medium is present in a liquid phase.

According to the invention, the reaction is carried out in the presence of an aromatic hydrocarbon which is liquid under the reaction conditions and has a boiling point from 80° to 240° C., in particular from 110° to 200° C. Preferred aromatic hydrocarbons comprise alkylbenzenes, in particular those which contain 1 or 2 alkyl groups of up to 6 carbon atoms. Particular preference is given to alkylbenzenes having 1 to 3 alkyl radicals of up to 4 carbon atoms in total. Suitable aromatic hydrocarbons are for example benzene, toluene, xylenes, ethylbenzene, diethylbenzene, trimethylbenzene, isopropylbenzene, propylbenzene and diisopropylbenzene.

The 6-aminocaproic acid used can be introduced into the reaction not only in a pure form but also in the form of a solution, for example in an alkanol or the aromatic hydrocarbon used as the reaction medium. If an alkanol is used as the solvent, it is advantageous to remove the alkanol from the system (for example by distillation) at the same rate as alcoholic solution of 6-aminocaproic ester is introduced, so as to prevent an accumulation of the alcohol.

Advantageously, the alkanol corresponds to the alcohol component of the 6-aminocaproic ester used, so that for example methanol will be used in the case of methyl 6-aminocaproate. Suitable solutions have a 6-aminocaproic ester content from 5 to 25% by weight.

Advantageously, from 2 to 20 kg of aromatic hydrocarbon reaction medium are present per kg of 6-aminocaproic ester.

Preferably, a residence time from 0.25 to 15 hours is maintained.

The reaction is carried out for example by heating a 6-aminocaproic ester, preferably with thorough mixing, in an aromatic hydrocarbon at the stated temperature, the pressure and temperature conditions having been selected in such a way as to ensure that the reaction medium is always present in the liquid state. Advantageously, the alcohol eliminated in the course of the heating is uninterruptedly removed from the reaction mixture, for example by distillation. Alternatively, the reaction is carried out for example by introducing a solution of a 6-aminocaproic ester in alkanol at the stated temperature into the aromatic hydrocarbon in a continuous manner until the desired concentration of 6-aminocaproic ester and caprolactam, for example from 5 to 25%, is obtained, while at the same time the alkanol used as the solvent and formed in the course of the cyclization is separated off by distillation. The reaction is then completed by further heating at the stated temperature while the alcohol freed in the course of the cyclization to caprolactam is advantageously removed by distillation.

In yet another preferred procedure, a solution of a 6-aminocaproic ester in the aromatic hydrocarbon used as the reaction medium is continuously charged to a cascade comprising a plurality, for example 2 to 4, of reaction vessels, any alkanol freed is separated off continuously, and from the last reaction vessel a solution of caprolactam is removed at a rate commensurate with that at which the starting solution is fed in. Alternatively, the alkanol is removed from the reaction mixture, for example by letting down, after the reaction has ended. This method is suitable when an aromatic hydrocarbon which contains a 6-aminocaproic ester is continuously charged to an elongated reaction zone, for example a tubular reactor or a tube coil, the reaction is carried out under the conditions stated above and the alcohol is separated off, for example by letting down or distillation, after the reaction mixture has been removed.

The caprolactam in the solution thus obtained with caprolactam in an aromatic hydrocarbon is generally isolated therefrom by fractional distillation, the aromatic hydrocarbon being recycled. Preferably, however, the caprolactam is extracted from the aromatic hydrocarbon with water. Advantageously, the extraction is carried out in countercurrent in conventional apparatus, for example mixer settlers, stirred disk columns or sieve plate columns with or without pulsation. Advantageously, the extraction is carried out at from 20° to 80° C. (If necessary, a bleed stream of the aromatic hydrocarbon is purified by distillation before reuse.)

The process of the invention is illustrated by reference to the following Examples.

EXAMPLE 1

A solution of 95.9 g (0.661 mol) of methyl 6-aminocaproate in 1,500 g of o-xylene is heated at 140° C. for 14 hours. The methanol formed is continuously removed by distillation. Removing the xylene by distillation under reduced pressure leaves 74.6 g (0.660 mol) of caprolactam; caprolactam yield: 99.8%.

EXAMPLE 2

A solution of 80.4 g (0.555 mol) of methyl 6-aminocaproate in 900 g of toluene is heated at 110° C. for 9 h with continuous removal of methanol-toluene mixture by distillation. Evaporation of the toluene under reduced pressure and purification by Sambay distillation at 120°–135° C. under 0.3 mbar leaves 56.8 g (0.503 mol); yield: 90.6%) of caprolactam.

EXAMPLE 3

A solution of 11.4 g (0.078 mol) of methyl 6-aminocaproate in 118 g of methanol is pumped at 130° C. and 4.0bar into a 250-ml glass autoclave filled with 279 g of benzene in the course of 4.5 h. 213 g of a methanolbenzene mixture are removed from the system by distillation at a rate commensurate with the rate of addition of methanolic methyl 6-aminocaproate solution and formation of methanol in the course of the cyclization to caprolactam. A further hour at 130° C. and evaporation of the benzene under reduced pressure leaves 8.6 g (0.076 mol; yield: 97.4%) of caprolactam.

EXAMPLE 4

A solution of 73.9 g (0.510 mol) of methyl 6-aminocaproate in 1,000 g of ethylbenzene is refluxed at 138° C. for 10 h. Methanol formed in the course of the reaction is removed by continuous distillation. Extracting the reaction solution with water and concentrating the aqueous phase under reduced pressure in a rotary evaporator leaves 54.0 g (0.047 mol; yield: 93.8%) of caprolactam.

EXAMPLE 5

65.3 g (0.450 mol) of methyl 6-aminocaproate are dissolved in 1,000 g of cumene, and the solution is heated at 150° C. for 10 h. Methanol formed is continuously removed by distillation. Evaporating off the cumene under reduced pressure leaves 48.5 g (0.429 mol; yield: 95.3%) of caprolactam.

EXAMPLE 6

A solution of 37.1 g (0.256 mol) of methyl 6-aminocaproate in 723 g of mesitylene is stirred under reflux at 140° C./500 bar for 12 h. Evaporating off the mesitylene under reduced pressure leaves 46.4 g of a caprolactam-acetylene mixture which, according to HPLC, contains 58.2% of caprolactam, which corresponds to 27.0 g (0.239 mol) and a yield of 93.4%.

EXAMPLE 7

In a first stage (stage 1 capacity: 800 ml; stage 2 capacity: 1,200 ml), 227 g of xylene and 200 g of a methanolic solution of 19.2 g (0.132 mol) of methyl 6-aminocaproate are pumped in per hour and heated to 140° C. Per hour, 211 g of a methanol-xylene mixture are distilled out of stage 1 via a 37-cm packed column. The solution thus obtained is continuously charged into a second stage and maintained at 140° C., and 215.9 g of a solution of caprolactam in xylene are discharged from stage 2. Removal of the xylene by distillation leaves 13.6 g (0.120 mol) of caprolactam and 0.8 g (0.005 mol) of methyl 6-aminocaproate per hour, which corresponds to a conversion of 96% and a selectivity of 94.5%.

EXAMPLE 8

In a three-stage cascade (stage 1 capacity: 800 ml, stage 2 capacity: 1,200 ml, stage 3 capacity: 600 ml), per hour 227 g of xylene and 200 g of a solution of 19.2 g (0.132 mol) of methyl 6-aminocaproate in methanol are pumped in and heated to 140° C. Per hour, 211 g of a methanol-xylene mixture are distilled out of stage 1 via a 37-cm packed column. The solution thus obtained is passed through two further stages at 140° C., and 215.9 g of a solution of caprolactam in xylene are discharged from stage 3. Removal of the xylene by distillation leaves 14.4 g (0.127 mol) of caprolactam and 0.3 g (0.002 mol) of methyl 6-aminocaproate per hour, which corresponds to a conversion of 98.4% and a selectivity of 97.7%.

EXAMPLE 9

Per hour, 230 g of xylene and 205 g of a solution of 18.5 g (0.128 mol) of methyl 6-aminocaproate in methanol are pumped into an 800-ml capacity stirred reactor and heated up to 140° C. Per hour, 216.4 g of a methanolxylene mixture are distilled off via a 37-cm packed column and 218.7 g of a solution of caprolactam in xylene are discharged. The latter solution is pumped through a tubular reactor at 270° C./27 bar with an average residence time of 45 min. Removal of the xylene by distillation leaves 13.8 g (0.122 mol) of caprolactam/hour, which corresponds to a yield of 95.3%.

EXAMPLE 10

A solution of 45.1 g (0.311 mol) of methyl 6-aminocaproate and 19.0 g (0.168 mol) of caprolactam in 700 g of o-xylene is pumped through a tubular reactor at 270° C./27 bar with an average residence time of 1.0 h. Removal of the xylene and methanol by distillation under reduced pressure leaves 0.8 g (0.006 mol) of methyl 6-aminocaproate and 52.2 g (0.462 mol) of caprolactam, which corresponds to a conversion of 98.1% and a selectivity of 96.4%.

COMPARATIVE EXAMPLE 1 (B510/1) (Stability of caprolactam in polyethylene glycol)

A solution of 20 g of caprolactam in 180 g of polyethylene glycol (HO—($CH_2$—$CH_2$—O)n—H; average molecular weight: 400) is stirred at 190° C. After 4 h the caprolactam content (monitored by HPLC) has decreased to 19.7%, after 7 h to 18.5%. A solution of 10 g of caprolactam in 190 g of polyethylene glycol (average molecular weight: 400) is stirred at 190° C. After 4 h the caprolactam content (monitored by HPLC) has decreased to 8.6%, after 7 h to 7.9%.

COMPARATIVE EXAMPLE 2

A solution of 63 g (0.434 mol) of methyl 6-aminocaproate and 33 g (0.292 mol) of caprolactam in 300 g of water is pumped at 275° C. through a 40-ml tubular reactor with an average residence time of 4 minutes. According to quantitative GC, the reaction solution contains 15% of caprolactam and, as a byproduct, 1% of N-methylcaprolactam. The caprolactam selectivity for a methyl 6-aminocaproate conversion of 100% is 54%.

COMPARATIVE EXAMPLE 3

A solution of 85.6 g (0.590 mol) of methyl 6-aminocaproate in 900 g of decalin is heated at the boil at 150° C. for 8 h. Methanol formed in the course of the cyclization is continuously removed by distillation. 2.6 g of polymer are precipitated in the course of the reaction. Evaporating the decal in under reduced pressure and Sambay distillation at 120°–135° C. under 0.3 mbar leaves 49.6 g (0.439 mol; yield: 74.4%) of caprolactam.

COMPARATIVE EXAMPLE 4

A solution of 110.5 g (0.762 mol) of methyl 6-aminocaproate in 1,032 g of dodecylbenzene (bp. 280° C.) is stirred at 180° C. for 4.5 h while the methanol formed is distilled off continuously. Extraction of the dodecylbenzene with water and removal of the water by distillation under reduced pressure leaves 76.3 g (0.675 mol; yield: 88.6%) of caprolactam.

We claim:

1. A process for preparing caprolactam by heating a 6-aminocaproic ester at 100°–320° C. in the presence of a reaction medium comprising an inert aromatic hydrocarbon which is liquid under reaction conditions and has a boiling point from 80° to 240° C., and isolating caprolactam from the reaction medium.

2. A process as claimed in claim 1, wherein the reaction medium used is an alkylbenzene having a boiling point from 110° to 200° C.

3. A process as claimed in claim 1, wherein an alkylbenzene having 1 to 3 alkyl radicals of up to 4 carbon atoms in total is used.

4. A process as claimed in claim 1, wherein a temperature from 130° to 280° C. is maintained.

5. A process as claimed in claim 1, wherein the alcohol obtained as an elimination product is separated off by distillation in the course of the reaction.

6. A process as claimed in claim 1, wherein the caprolactam is separated from the aromatic hydrocarbon by extraction with water.

7. A process as claimed in claim 1, wherein the starting compound used is methyl 6-aminocaproate or ethyl 6-aminocaproate.

* * * * *